United States Patent [19]

Jolly et al.

[11] 4,435,325

[45] Mar. 6, 1984

[54] 1α,25α-DIHYDROXY-CHOLECALCIFEROL AND METHODS FOR THE PRODUCTION THEREOF

[75] Inventors: Jean Jolly, Fontenay-sous-Bois; Primo Rizzi, Villemomble; Jean Taillardat, Domont, all of France

[73] Assignee: Roussel Uclaf, Paris, France

[21] Appl. No.: 146,497

[22] Filed: May 5, 1980

[30] Foreign Application Priority Data

May 23, 1979 [FR] France .................................. 79 13118

[51] Int. Cl.³ ........................... C07J 71/00; C07J 5/00
[52] U.S. Cl. .................................. 260/397.2; 424/236
[58] Field of Search ...................... 260/397.2; 424/236

[56] References Cited

U.S. PATENT DOCUMENTS

| | | | |
|---|---|---|---|
| 3,665,020 | 5/1972 | Marbet | 260/397.2 |
| 3,833,622 | 9/1974 | Babcock et al. | 260/397.2 |
| 3,993,675 | 11/1976 | Uskokovic et al. | 260/397.2 |
| 4,022,768 | 5/1977 | Matsunaga et al. | 260/397.2 |

*Primary Examiner*—Elbert L. Roberts
*Attorney, Agent, or Firm*—Hammond & Littell, Weissenberger and Muserlian

[57] ABSTRACT

The monohydrate of 1α,25-dihydroxy-cholecalciferol having a remarkable vitamin activity and a process for its preparation.

4 Claims, No Drawings

1α,25α-DIHYDROXY-CHOLECALCIFEROL AND METHODS FOR THE PRODUCTION THEREOF

STATE OF THE ART

1α,25-dihydroxy-cholecalciferol is a known compound of the formula

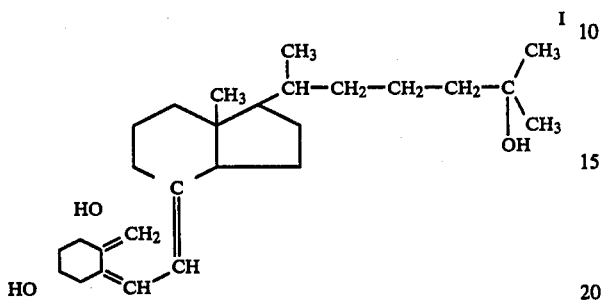

and is described in U.S. Pat. No. 3,697,559 and French Pat. No. 2,213,053 as possessing a remarkable vitamin activity. The said product, due to its elaborate structure, is prepared by a relatively long and expensive synthesis resulting in a difficult-to-crystallize product not suitable for pharmaceutical use. For example, French Pat. No. 2,213,053 describes a chloroform solvate of 1α,25-dihydroxy-cholecaliferol but one tries to avoid where possible the use of chloroform in pharmaceutical specialities. One can also cite French Pat. No. 2,301,503, U.S. Pat. No. 4,022,768 and Chem. Abst. Vol. 83 No. 15, 1975, 131,828n p. 534.

OBJECTS OF THE INVENTION

It is an object of the invention to provide the novel monohydrate of 1α,25-dihydroxy-cholecalciferol and to provide a novel process for its preparation.

It is another object of the invention to provide a novel vitamin composition and a novel method of increasing intestinal absorption of calcium and fixation of calcium.

These and other objects and advantages of the invention will become obvious from the following detailed description.

THE INVENTION

The novel product of the invention is the monohydrate of 1α,25-dihydroxy-cholecalciferol which is perfectly crystalline, very stable and is easily obtained in a pure form and meets the requirements of modern theraphy. The presence of water in the molecule does not cause any troublesome side effects when the product is administered to a living organism. Moreover, the product of the invention may be prepared from amorphus 1α,25-dihydroxy-cholecalciferol or the solvates of the prior art, especially that produced by French Pat. No. 2,213,053 with excellent yields.

The process of the invention for the preparation of the monohydrate of 1α,25-dihydroxy-cholecalciferol comprises forming a solution of 1α,25-dihydroxy-cholecalciferol or a solvate thereof in an organic solvent and adding water to the solution to form crystalline monohydrate of 1α,25-dihydroxy-cholecalciferol which is easily recovered.

Examples of suitable organic solvents are acetone and lower alkanols such as methanol or ethanol although the preferred solvent is acetone. Preferably the starting solvate will be desolvated by dissolution in an appropriate solvent. If the solvate is solvated with choloroform, the preferred solvent for desolvation is an ether such as ethyl ether.

The novel vitamin composition of the invention is comprised of an effective amount of crystalline monohydrate of 1α,25-dihydroxy-cholecalciferol and an inert pharmaceutical carrier. The composition may be in the form of tablet, dragees, gelules, granules, suppositories and injectable solutions or suspensions.

Examples of suitable excipients for the compositions are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

The compositions have remarkable vitamin properties and favor intestinal absorption of calcium and calcium fixation in osteoid tissue and are useful for treating rachitism, hypocalcemia, osteomalacia and spasmophilia.

The novel method of the invention for increasing intestinal absorption of calcium and calcium fixation in osteoid tissue in warm-blooded animals, including humans, comprises administering to warm-blooded animals an amount of the monohydrate of 1α,25-dihydroxy-cholecalciferol sufficient to increase calcium intestinal absorption. The said product may be administered orally, rectally or parenterally. The usual dail dose is depending on the method of administration, for example, it can be comprised between 0,002 and 4 μg by oral route in the adult.

In the following examples there are described several preferred embodiments to illustrate the invention. However, it should be understood that the invention is not intended to be limited to the specific embodiments.

EXAMPLE 1

1.585 g of 1α,25-dihydroxy-cholecaliferol (solvated with chloroform produced by Example 7 of French Pat. No. 2,213,053) were dissolved at 20° C. in 16 volumes of ethyl ether and the suspension of slight insolubles was filtered. The filtrate was evaporated to dryness under reduced pressure at low temperatures to obtain a white powder which was dissolved at 20° C. in 18 volumes of acetone. 27 volumes of water were added to the solution at 20° C. and the mixture was stirred at 18°–20° C. for one hour and then allowed to stand for 2 hours. The mixture was vacuum filtered and the product was washed with water and taken up in water. The mixture stood for 30 minutes at room temperature and was vacuum filtered to obtain 3.405 g of product which was dried in the presence of potassium hydroxide to obtain 1.252 g of product which was completely hydrated in 90 minutes to obtain the monohydrate of 1α,25-dihydroxy-cholecalciferol in the form of a white powder free of choloroform and containing 4.1% by weight of water. The product had a specific rotation of $[\alpha]_D^{20} = +47°$ (c=0.5% in ethanol).

U.V. Spectrum (95% ethanol): at 265 nm, $E_1^1 = 412$

NMR Spectrum (CDCl$_3$-60MHz): Peaks at 0.55 ppm (18-CH$_3$); at 1.22 ppm (26-CH$_3$ and 27-CH$_3$); at 19 to 5 and 5.3 ppm (19-CH$_2$); at 6.04 ppm and 6.45 ppm (6- and 7-hydrogens); at 1.5 ppm (presence of water).

EXAMPLE 2

Capsules were prepared containing 0.25 μg, 0.5 μg and 1 μg of monohydrate of 1α,25-dihydroxy-cholecalciferol and sufficient sterile oil excipient to fill the capsules.

Various modifications of the product or processes of the invention may by made without departing from the spirit or scope thereof and it should be understood that the invention is to be limited only as defined in the appended claims.

We claim:

1. A process for the preparation of the product of claim 1 comprising dissolving a chloroform solvate of 1α,25-dihydroxy-cholecaliferol in an organic solvent to effect desolvation and adding water to the solution to crystallize the monohydrate.

2. The process of claim 1 wherein the solvent is acetone.

3. The process of claim 1 wherein the solvent for desolvation is an ether.

4. The process of claim 1 wherein the solvent for desolvation is ethyl ether.

* * * * *